United States Patent [19]
Boltri et al.

[11] Patent Number: 5,858,330
[45] Date of Patent: *Jan. 12, 1999

[54] PHARMACEUTICAL FORMULATIONS IN FORM OF THIXOTROPIC GEL

[75] Inventors: Luigi Boltri; Antonietta Coppola; Marco Gentile; Gaetano Clavenna, all of Milan, Italy

[73] Assignee: Dompe' S.p.A., L'Aquila, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 617,205

[22] Filed: Mar. 18, 1996

[30] Foreign Application Priority Data

Mar. 22, 1995 [IT] Italy ................................ MI95A0568

[51] Int. Cl.$^6$ ....................................................... A61L 9/04

[52] U.S. Cl. ............................. 424/45; 424/450; 424/484; 424/401; 514/772

[58] Field of Search ............................. 424/45, 450, 484; 514/772

[56] References Cited

U.S. PATENT DOCUMENTS 4,992,256  2/1991  Skaggs ....................................... 424/45
4,996,240  2/1991  Osipow et al. .

*Primary Examiner*—Rebecca Cook
*Attorney, Agent, or Firm*—Griffin, Butler, Whisenhunt & Szipl, LLP

[57] ABSTRACT

The present invention relates to a topical formulation of gel-like consistency, but nebulizable by a mechanical pump, containing colloidal silices as gelifying agent.

9 Claims, No Drawings

PHARMACEUTICAL FORMULATIONS IN FORM OF THIXOTROPIC GEL

The present invention relates to a topical formulation of gel-like consistency, but nebulizable by mechanical pump, containing colloidal silices as gelifying agent.

PRIOR ART

The preparation of a semi-solid system nebulizable by means of a spray mechanical system seemed up to now to be an unsurmountable problem. In fact, efforts to prepare formulations making use of the conventional, most used gelifying agents lead to the production of gels which, although being highly valid, are absolutely not sprayable. Even making a compromise, namely decreasing the system viscosity, at the most the emission of the product from the mechanical pump is obtained, but not the nebulization. Moreover, decreasing viscosity, the product tends to leak once sprayed on the concerned part.

In the cosmetic field, the so-called gel-sprays exist, which however have an exceedingly low viscosity, thereby tending to leak after the emission, therefore they cannot be even defined gels. Moreover they are usually prepared using acrylates such as Carbopols.

DISCLOSURE OF THE INVENTION

The present invention overcomes the problems of the prior art, by the use of a high viscosity system, which is nearly semisolid, characterized in that it is destructurated by a mechanical stress The pharmaceutical formulations in form of thixotropic gel of the present invention will contain, besides an active ingredient, a colloidal silica in an amount from 2 to 15% by weight, propylene glycol in an amount from 1 to 10% by weight. Water and any excipients conventionally used in the pharmaceutical techniques, such as surfactants, preservatives, flavouring agents, co-solvents and lipophilic phases can also be present. Particularly preferred surfactants are those belonging to the following classes:

Sorbitan esters (for example Span 20, Span 40, Span 60, Span 65, Span 80, Span 85);

Polyoxyethylene sorbitan esters (for example Tween 80, Tween 60, Tween 40, Tween 20);

Polyoxyethylalkyl ethers (for example Cremophor A, Bryj, Texofor A);

Polyoxyethylene stearates (for example Myrj 52, Myrj 53).

The pharmaceutical formulations of the invention will preferably contain a colloidal silica having a surface area of 175–225 $m^2/g$ and an average diameter of 12 nm, in amounts ranging from 2 to 8%, more preferably from 2.5 to 7% by weight.

In the pharmaceutical formulations of the invention, water may be present in an amount ranging from 60 to 97% by weight.

The present invention provides a system characterized by:

Pseudoplasticity: the viscosity decreases with the increase in the intensity of the applied stress;

Thixotropy: the viscosity decreases with time, as the applied stress goes on.

The system of the present invention uses as gelifying agent colloidal silices, which are excipients widely used in the topical field as thickening and suspending agents, and in the oral solid as lubricants.

It should be noted that within the definition "colloidal silica" lie several commercial products used as pharmaceutical excipients, whose characteristics can be summarized as follows:

Surface area from 50 to 400 $m^2/g$

Average diameter from 7 to 40 nm.

All of these materials give similar gelification phenomena but, since gelification occurs through adsorption, the surface area characteristics become paramount for the choice of the type and amount of colloidal silica to use.

Suitable silices according to the invention have a surface area ranging from 130 to 300 $m^2/g$ and an average diameter of 12 nm.

The present invention uses specifically as colloidal silices Aerosils, preferably colloidal silices with characteristics similar to Aerosil 200.

Aerosil characteristics of pseudoplasticity and thixotropy are well known, however up to now said characteristics have not been made use of in order to spray/nebulize a product in the form of gel by the simple pressure of a finger.

In essentially aqueous systems, aerosils (only) at high concentrations (5–15%) cause the structuration of water through adsorption phenomena, until a consistence of gel (or, more correctly, magma). The Aerosil-Water bond is very mild and it can be cleaved by even slight stresses, such as those caused by a mechanical pump. During the stress, and therefore during the spray, the viscosity of the system remarkably decreases, thereby allowing the nebulization. Once applied to the skin, the sprayed product, no longer stressed, quickly returns to its original state, acquiring back a gel-like consistence.

It is particularly surprising that, when in the formulation of the invention besides Aerosil and water, a less polar solvent is also present, such as glycerol, polyoxyethylene glycol, diethylene glycol monoalkyl ether (Transcutol™), N-methylpyrrolidone, glycofurol, isopropanol, ethylene glycol, propylene glycol, viscosity falls upon the slightest mechanical stress; in the absence of said solvent, such a phenomenon appears less markedly, but anyhow so as not to affect adversely the thixotropic characteristics according to the invention. The use of the propylene glycol is particularly preferred.

The topical gel formulation of the present invention can be administered with a suitable dosage, through doser mechanical pumps which dispense prefixed volumes.

The topical formulations of the present invention can be used, besides for the topical administration on the skin, also for the vaginal, nasal, otological administration, wherein the absence of leakage and the in loco persistence are particularly important.

The gels of the present invention will preferably be dispensed by means of mechanical pump dispensers.

The formulations of the invention can also contain all of the active ingredients whose topical administration is therapeutically effective. Examples of active ingredients which can be used in the formulations of the invention comprise: non-steroidal antiinflammatory agents, such as ketoprofen, ibuprofen (including optical isomers and salts thereof), naproxen, diclofenac, diflunisal, nimesulide, ketorolac, flurbiprofen, indomethacin, acetylsalicylic acid and the like; antifungal drugs such as miconazole, econazole, fluconazole, tyrothricin, antibacterials/antibiotics such as polymyxin, neomycin, kanamycin, gentamycin, tetracycline, meclocycline, clindamycin; antiviral drugs such as acyclovir, cytarabine; corticosteroids; antihistamines; sympathomimetic drugs; antiallergic drugs such as disodium cromoglycate; local anesthetics; cicatrizants; capillary-protective substances; bioflavonoids; retinoids; vitamins; enzymes; growth factors.

Some examples of pharmaceutical and parapharmaceutical formulations containing active ingredients at therapeutical concentrations are reported hereinbelow.

a.i.=active ingredient

PHARMACEUTICAL FORMULATIONS

EXAMPLE 1

| a.i. | Ketoprofen Lys | 15 g |
| --- | --- | --- |
| | colloidal silica | 5 g |
| | propylene glycol | 5 g |
| | Tween 80 | 0.5 g |
| | Na nipagin | 0.1 g |
| | Nerolene lavender | 0.1 g |
| | demin. water q.s. to | 100 g |

EXAMPLE 2

| a.i. | miconazole nitrate | 2 g |
| --- | --- | --- |
| | propylene glycol | 10 g |
| | colloidal silica | 3 g |
| | esterified polyoxyethylene glycols | 3 g |
| | polysorbate 80 | 0.5 g |
| | sodium methyl-p-hydroxybenzoate | 0.15 g |
| | malva perfume | 0.5 g |
| | demin. water q.s. to | 100 g |

EXAMPLE 3

| a.i. | disodium cromoglycate | 4 g |
| --- | --- | --- |
| | propylene glycol | 5 g |
| | colloidal silica | 5.5 g |
| | sodium edetate | 10 mg |
| | polysorbate 80 | 0.5 g |
| | benzalkonium chloride | 10 mg |
| | menthol | 0.3 g |
| | eucalyptol | 0.1 g |
| | demin. water q.s. to | 100 g |

EXAMPLE 4

| a.i. | oxymetazoline hydrochloride | 0.050 g |
| --- | --- | --- |
| | monobasic sodium phosphate | 1.020 g |
| | dibasic sodium phosphate | 1.110 g |
| | EDTA | 0.010 g |
| | propylene glycol | 5.0 g |
| | colloidal silica | 5.0 g |
| | Tween 20 | 0.5 g |
| | sodium methyl-p-hydroxybenzoate | 0.15 g |
| | menthol | 0.4 g |
| | eucalyptol | 0.1 g |
| | demin. water q.s. to | 100 g |

EXAMPLE 5

| a.i. | menthol | 0.4 g |
| --- | --- | --- |
| | camphor | 0.4 g |
| | eucalyptol | 0.2 g |
| | sodium phosphate monobasic | 1.02 g |
| | sodium phosphate dibasic | 1.11 g |
| | EDTA | 0.01 g |
| | propylene glycol | 8.0 g |
| | colloidal silica | 4.0 g |
| | polysorbate 80 | 1.0 g |
| | sodium methyl-p-hydroxybenzoate | 0.15 g |
| | demin. water q.s. to | 100 g |

EXAMPLE 6

| a.i. | tyrothricin | 0.02 g |
| --- | --- | --- |
| | cethyltrimethylammonium bromide | 0.05 g |
| | benzocaine | 0.05 g |
| | PEG 200 | 4 g |
| | colloidal silica | 4 g |
| | ethyl alcohol | 5 g |
| | Cremophor A11 | 0.7 g |
| | sodium saccharine | 0.02 g |
| | sodium methyl-p-hydroxybenzoate | 0.15 g |
| | peppermint Oil | 0.5 g |
| | demin. water q.s. to | 100 g |

EXAMPLE 7

| a.i. | polymixin B sulfate | 1.000.000 I.U. |
| --- | --- | --- |
| | neomycin sulfate | 0.5 g |
| | lidocaine chloride | 4 g |
| | propylene glycol | 10 g |
| | colloidal silica | 3 g |

-continued

| | polysorbate 80 | 0.5 g |
| --- | --- | --- |
| | sodium methyl-p-hydroxybenzoate | 0.15 g |
| | rose essence | 0.2 g |
| | demin. water q.s. to | 100 g |

EXAMPLE 8

| a.i. | fluocinolone acetonide | 0.025 g |
| --- | --- | --- |
| | propylene glycol | 10 g |
| | colloidal silica | 4 g |
| | gliceryl monostearate self-emulsifier | 4 g |
| | Span 60 | 0.5 g |
| | sodium methyl-p-hydroxybenzoate | 0.15 g |
| | lavender essence | 0.2 g |
| | demin. water q.s. to | 100 g |

EXAMPLE 9

| a.i. | betametasone valerate | 0.1 g |
| --- | --- | --- |
| | propylene glycol | 5 g |
| | colloidal silica | 5 g |
| | isopropyl alcohol | 5 |
| | polysorbate 80 | 0.5 g |
| | sodium methyl-p-hydroxybenzoate | 0.15 g |
| | lavender essence | 0.1 g |
| | demin. water q.s. to | 100 g |

EXAMPLE 10

| a.i. | meclocycline anhydrous sulfosalicylate | 2.914 g |
| --- | --- | --- |
| | propylene glycol | 4 g |
| | glycerin U.P. | 1 g |
| | colloidal silica | 3.5 g |
| | esterified polyoxyethylene glycols | 3 g |
| | polysorbate 80 | 0.5 g |
| | sodium methyl-p-hydroxybenzoate | 0.15 g |
| | rose essence | 0.2 g |
| | demin. water q.s. to | 100 g |

EXAMPLE 11

| a.i. | naproxene | 10 g |
| --- | --- | --- |
| | colloidal silica | 5 g |
| | ethyl alcohol | 10 g |
| | polysorbate 80 | 0.75 g |
| | sodium methyl-p-hydroxybenzoate | 0.15 g |
| | camphor | 0.2 g |
| | demin. water q.s. to | 100 g |

EXAMPLE 12

| a.i. | escin | 2 g |
| --- | --- | --- |
| | sodium heparin | 5.000 I.U. |
| | diethylamine salicylate | 5 g |
| | transcutol | 2 g |
| | colloidal silica | 6 g |
| | ethyl alcohol | 10 g |
| | polysorbate 80 | 0.50 g |
| | sodium methyl-p-hydroxybenzoate | 0.15 g |
| | camphor | 0.05 g |
| | lavender essence | 0.05 g |
| | demin. water q.s. to | 100 g |

EXAMPLE 13

| a.i. | capsaicin oleoresin 1 g (= 0.01 g capsaicin) | 2 g |
| --- | --- | --- |
| | propylene glycol | 1 g |
| | colloidal silica | 5 g |
| | ethyl alcohol | 2 g |
| | polyoxyethylen glycol 300 | 5 g |
| | polysorbate 80 | 0.80 g |
| | sodium methyl-p-hydroxybenzoate | 0.15 g |
| | camphor | 0.2 g |
| | menthol | 0.2 g |
| | demin. water q.s. to | 100 g |

EXAMPLE 14

| a.i. | sodium heparin | 5.000 U.E.B. |
| --- | --- | --- |
| | ethyl alcohol | 10 g |
| | propylene glycol | 10 g |
| | colloidal silica | 6 g |
| | polysorbate 80 | 0.50 g |
| | sodium methyl-p-hydroxybenzoate | 0.15 g |
| | camphor | 0.6 g |
| | demin. water q.s. to | 100 g |

EXAMPLE 15

| a.i. | sodium heparin | 10.000 | I.U. |
| --- | --- | --- | --- |
| | escin | 1 | g |
| | phosphatidyl choline | 0.8 | g |
| | isopropyl alcohol | 15 | g |
| | propylene glycol | 5 | g |
| | colloidal silica | 6 | g |
| | polysorbate 80 | 1 | g |
| | sodium methyl-p-hydroxybenzoate | 0.15 | g |
| | lavender essence | 0.1 | g |
| | demin. water q.s. to | 100 | g |

EXAMPLE 16

| a.i. | sodium heparin | 5.000 | U.E.B. |
| --- | --- | --- | --- |
| | jalurononidase | 5.000 | I.U. |
| | desametasone | 0.05 | g |
| | tetracaine hydrochloride | 0.1 | g |
| | retinol palmitate | 25.000 | I.U. |
| | ethyl alcohol | 2 | g |
| | colloidal silica | 3 | g |
| | propylene glycol | 10 | g |
| | Myrj 52 | 1 | g |
| | sodium methyl-p-hydroxybenzoate | 0.15 | g |
| | menthol | 0.1 | g |

EXAMPLE 17

| a.i. | hydrocortisone acetate | 0.5 | g |
| --- | --- | --- | --- |
| | benzocaine | 5 | g |
| | sodium heparin | 5.000 | I.U. |
| | colloidal silica | 5 | g |
| | propylene glycol | 7 | g |
| | isopropyl myristate | 3 | g |
| | polysorbate 80 | 1 | g |
| | sodium methyl-p-hydroxybenzoate | 0.15 | g |
| | menthol | 0.25 | g |
| | demin. water q.s. to | 100 | g |

EXAMPLE 18

| a.i. | Hamamelis hydroalcoholic extract | 0.75 | g |
| --- | --- | --- | --- |
| | tannic acid | 5 | g |
| | benzalkonium chloride | 1 | g |
| | ethyl alcohol | 4 | g |
| | propylene glycol | 5 | g |
| | colloidal silica | 5 | g |
| | Cetomacrogol 1000 | 0.5 | g |
| | sodium methyl-p-hydroxybenzoate | 0.15 | g |
| | bergamot oil | 0.1 | g |
| | demin. water q.s. to | 100 | g |

EXAMPLE 19

| a.i. | chlorhexidine | 1 | g |
| --- | --- | --- | --- |
| | ethyl alcohol | 3 | g |
| | isopropyl myristate | 4 | g |
| | propylene glycol | 2 | g |
| | colloidal silica | 3 | g |
| | polysorbate 80 | 0.5 | g |
| | sodium methyl-p-hydroxybenzoate | 0.15 | g |
| | bergamot oil | 0.1 | g |
| | demin. water q.s. to | 100 | g |

EXAMPLE 20

| a.i. | benzyl alcohol | 4 | g |
| --- | --- | --- | --- |
| | benzocaine | 5 | g |
| | chloroxylenol | 0.5 | g |
| | ethyl alcohol | 5 | g |
| | propylene glycol | 8 | g |
| | colloidal silica | 5 | g |
| | Bryj 35 | 0.5 | g |
| | sodium methyl-p-hydroxybenzoate | 0.15 | g |
| | bergamot oil | 0.1 | g |
| | demin. water q.s. to | 100 | g |

EXAMPLE 21

| a.i. | acyclovir | 5 | g |
| --- | --- | --- | --- |
| | ethyl alcohol | 5 | g |
| | propylene glycol | 10 | g |
| | colloidal silica | 5 | g |
| | polysorbate 80 | 0.5 | g |
| | sodium methyl-p-hydroxybenzoate | 0.15 | g |
| | peppermint oil | 0.3 | g |
| | demin. water q.s. to | 100 | g |

EXAMPLE 22

| a.i. | escin | 0.3 | g |
| --- | --- | --- | --- |
| | levothyroxine | 0.05 | g |
| | ethyl alcohol | 10 | g |
| | propylene glycol | 2 | g |
| | colloidal silica | 3.5 | g |
| | esterified polyeoxyethylene glycols | 3 | g |
| | polysorbate 80 | 1 | g |
| | sodium methyl-p-hydroxybenzoate | 0.15 | g |
| | lily of the valley essence | 0.3 | g |
| | demin. water q.s. to | 100 | g |

EXAMPLE 23

| a.i. | vitamin E | 550 | I.U. |
| --- | --- | --- | --- |
| | propylene glycol | 1 | g |
| | Jojoba oil | 1 | g |
| | colloidal silica | 3 | g |
| | anhydrous lanolin | 1 | g |
| | Labrafil M1944 CS | 3 | g |
| | polyoxyethylene glycol palmitostearate | 2 | g |
| | Tween 20 | 0.75 | g |
| | sodium methyl-p-hydroxybenzoate | 0.15 | g |
| | rose perfume | 0.5 | g |
| | demin. water q.s. to | 100 | g |

EXAMPLE 24

| a.i. | beclometasone dipropionate | 10 | mg |
| --- | --- | --- | --- |
| | propylene glycol | 10 | g |
| | colloidal silica | 3.5 | g |
| | polysorbate 80 | 0.7 | g |
| | sodium methyl-p-hydroxybenzoate | 0.15 | g |
| | menthol | 0.3 | g |
| | camphor | 0.2 | g |
| | demin. water q.s. to | 100 | g |

EXAMPLE 25

| a.i. | 2,4-dichlorobenzyl alcohol | 600 | mg |
| --- | --- | --- | --- |
| | propylene glycol | 6 | g |
| | colloidal silica | 3 | g |
| | ethyl alcohol | 10 | g |
| | polysorbate 80 | 0.5 | g |
| | sodium saccharine | 0.03 | g |
| | sodium methyl-p-hydroxybenzoate | 0.15 | g |
| | mint essence | 0.3 | g |
| | menthol | 100 | mg |
| | balsamic flavor | 1 | g |
| | demin. water q.s. to | 100 | g |

EXAMPLE 26

| a.i. | thiocolchicoside | 0.25 | g |
| --- | --- | --- | --- |
| | propylene glycol | 7 | g |
| | colloidal silica | 3.5 | g |
| | 70% sorbitol | 5.0 | g |
| | polysorbate 80 | 0.5 | g |
| | sodium methyl-p-hydroxybenzoate | 0.15 | g |
| | lavender essence | 0.5 | g |
| | demin water q.s. to | 100 | g |

EXAMPLE 27

| a.i. | ketoprofene lysine salts | 15 | g |
| --- | --- | --- | --- |
| | propylene glycol | 5.5 | g |
| | colloidal silica | 2.5 | g |
| | polysorbate 80 | 0.5 | g |
| | methyl-p-hydroxybenzoate | 0.15 | g |
| | camphor | 0.1 | g |
| | lavender essence | 0.1 | g |
| | demin. water q.s. to | 100 | g |

EXAMPLE 28

| a.i. | sodium heparin | 10000 | I.U. |
| --- | --- | --- | --- |
| | propylene glycol | 5 | g |
| | colloidal silica | 3.5 | g |
| | 70% sorbitol | 8 | g |
| | polysorbate 80 | 0.5 | g |
| | methyl-p-hydroxybenzoate | 0.15 | g |
| | nerolene lavender | 0.2 | g |
| | demin. water q.s. to | 100 | g |

EXAMPLE 29

| | | |
|---|---|---|
| a.i. | benzalkonium chloride | 1 g |
| | propylene glycol | 5 g |
| | colloidal silica | 3.5 g |
| | polysorbate 80 | 0.5 g |
| | methyl-p-hydroxybenzoate | 0.15 g |
| | lavender essence | 0.2 g |
| | lemon essence | 0.4 g |
| | demin. water q.s. to | 100 g |

EXAMPLE 30

| | | |
|---|---|---|
| a.i. | deschlorpheniramine maleate | 1 g |
| | ethyl alcohol | 3 g |
| | propylene glycol | 5 g |
| | gliceryl monostearate self-emulsifier | 5 g |
| | 70% sorbitol | 5 g |
| | colloidal silica | 3.5 g |
| | polysorbate 80 | 0.7 g |
| | methyl-p-hydroxybenzoate | 0.15 g |
| | rose essence | 0.1 g |
| | demin. water q.s. to | 100 g |

EXAMPLE 31

| | | |
|---|---|---|
| a.i. | metronidazole | 1 g |
| | ethyl alcohol | 5 g |
| | propylene glycol | 10 g |
| | colloidal silica | 3.0 g |
| | polysorbate 80 | 1 g |
| | methyl-p-hydroxybenzoate | 0.15 g |
| | lily of the valley essence | 0.5 g |
| | demin. water. q.s. to | 100 g |

PARA-PHARMACEUTICAL FORMULATIONS

EXAMPLE 32
Facial astringent masque

| | | |
|---|---|---|
| a.i. | Hamamelis hydroalcoholic extract | 5 g |
| | nettle oily extract | 2 g |
| | propylene glycol | 5 g |
| | colloidal silica | 5 g |
| | polysorbate 60 | 1 g |
| | sodium methyl-p-hydroxybenzoate | 0.15 g |
| | lemon essence | 0.07 g |
| | demin. water q.s. to | 100 g |

EXAMPLE 33
Sun shield gel

| | | |
|---|---|---|
| a.i. | β carotene solution in vegetable oil | 3 g |
| | Hypericum oily extract | 2 g |
| | propylene glycol | 2 g |
| | colloidal silica | 5 g |
| | polysorbate 80 | 1 g |
| | sodium methyl-p-hydroxybenzoate | 0.15 g |
| | sandalwood essence | 0.1 g |
| | demin. water q.s. to | 100 g |

EXAMPLE 34
Face spray gel detergent

| | | |
|---|---|---|
| a.i. | sulfur glycolic solution | 1 g |
| | benzoyl peroxide | 4 g |
| | isopropyl alcohol | 4 g |
| | propylene glycol | 10 g |
| | colloidal silica | 5 g |
| | polysorbate 80 | 0.7 g |
| | sodium methyl-p-hydroxybenzoate | 0.15 g |
| | rose essence | 0.3 g |
| | demin. water q.s. to | 100 g |

EXAMPLE 35
Astringent facial masque

| | | |
|---|---|---|
| a.i. | Burdock hydroalcoholic extract | 1 g |
| | Cornflower hydroalcoholic extract | 1 g |
| | propylene glycol | g |
| | colloidal silica | 3.5 g |
| | polysorbate 80 | 0.5 g |
| | methyl-p-hydroxybenzoate | 0.15 g |
| | apricot flavour | 0.2 g |
| | demin. water q.s. to | 100 g |

EXAMPLE 36
Face detergent

| | | |
|---|---|---|
| a.i. | Ruscus hydroalcoholic extract | 1 g |
| | Asparagus hydroalcoholic extract | 1 g |
| | propylene glycol | 5 g |
| | colloidal silica | 3 g |
| | polysorbate 80 | 0.5 g |
| | methyl-p-hydroxybenzoate | 0.15 g |
| | rose essence | 0.3 g |
| | demin. water q.s. to | 100 g |

We claim:

1. A pharmaceutical thixotropic gel composition comprising an active ingredient, from 2 to 15% of a colloidal silica having a surface area ranging from 130 to 300 $m^2/g$, water in an amount of from 60 to 97% by weight and, optionally, one or more excipients.

2. The pharmaceutical composition according to claim 1 further comprising a solvent selected from glycerol, polyoxyethylene glycol, diethylene glycol monoalkyl ether, N-methylpyrrolidone, glycofurol, isopropanol, ethylene glycol, propylene glycol in an amount from 1 to 10% by weight.

3. The pharmaceutical composition according to claim 2, wherein the solvent is propylene glycol.

4. The pharmaceutical composition according to claim 1, wherein the colloidal silica has an average diameter of 12 nm.

5. The pharmaceutical composition according to claim 1, wherein the colloidal silica has a surface area ranging from 200–250 $m^2/g$ and an average diameter of 12 nm.

6. The pharmaceutical composition according to claim 1 wherein the one or more excipients is selected from a surfactant, a preservative, a flavouring agent, a co-solvent and a lipophilic phase.

7. The pharmaceutical composition according to claim 1, further comprising a surfactant selected from the group consisting of a sorbitan ester, a polyoxyethylene sorbitan ester, a polyoxyalkyl ether, and a polyoxyethylene stearate.

8. A composition according to claim 1, containing from 2 to 7% by weight of colloidal silica.

9. A container having a mechanical spray pump and comprising the composition of claim 1.

* * * * *